US009497983B2

(12) United States Patent
Minor et al.

(10) Patent No.: US 9,497,983 B2
(45) Date of Patent: Nov. 22, 2016

(54) LIQUID ENTERAL NUTRITIONAL COMPOSITION WITH A LOW MONOVALENT METAL ION CONTENT

(75) Inventors: Marcel Minor, Wageningen (NL); Suzanne van Steenis, Wageningen (NL); Hilde Ruis, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 18 days.

(21) Appl. No.: 13/376,098

(22) PCT Filed: Jun. 7, 2010

(86) PCT No.: PCT/NL2010/050345
§ 371 (c)(1),
(2), (4) Date: Feb. 21, 2012

(87) PCT Pub. No.: WO2010/140891
PCT Pub. Date: Dec. 9, 2010

(65) Prior Publication Data
US 2012/0142587 A1    Jun. 7, 2012

(30) Foreign Application Priority Data
Jun. 5, 2009  (WO) ............... PCT/NL2009/050313

(51) Int. Cl.
| A61K 38/17 | (2006.01) |
| A61K 38/16 | (2006.01) |
| A61P 1/00 | (2006.01) |
| A23L 1/305 | (2006.01) |
| A23L 1/29 | (2006.01) |
| A23L 1/304 | (2006.01) |

(52) U.S. Cl.
CPC ............ *A23L 1/305* (2013.01); *A23L 1/296* (2013.01); *A23L 1/304* (2013.01); *A23L 1/3056* (2013.01)

(58) Field of Classification Search
USPC ........................................................ 514/5.6
See application file for complete search history.

(56) References Cited

U.S. PATENT DOCUMENTS

| 5,503,865 | A | 4/1996 | Behringer et al. |
| 5,639,502 | A | 6/1997 | Behringer et al. |
| 5,683,984 | A | 11/1997 | Jost |
| 7,887,864 | B2 * | 2/2011 | Cale et al. ............ 426/330.2 |
| 2006/0088574 | A1 * | 4/2006 | Manning et al. ......... 424/439 |

FOREIGN PATENT DOCUMENTS

| EP | 0 686 396 A1 | 12/1995 |
| EP | 1 563 741 A1 | 8/2005 |
| NZ | 555477 A | 6/2008 |
| WO | WO-98/18350 A1 | 5/1998 |
| WO | WO-2005/096845 | 10/2005 |
| WO | WO-2007/108827 A1 | 9/2007 |
| WO | WO-2008/041219 A1 | 4/2008 |
| WO | WO-2009/059266 A1 | 5/2009 |
| WO | WO-2009/072886 A1 | 6/2009 |
| WO | WO-2010/140877 A1 | 12/2010 |

OTHER PUBLICATIONS

Anonymous, "Muscle Milk: Nature's Ultimate Growth Formula," Internet Citation, Jul. 23, 2003, pp. 1-3, XP002516238, Retrieved from the Internet: URL:http://www.1fast400.com/p433_Mass_Maker_Beverly_International.html, [retrieved on Feb. 20, 2009].
Search Report in International Application No. PCT/NL2010/050345 dated Jan. 4, 2011.
"Food Processing", Feb. 1995.
Bienvenue et. al., "Rheological properties of concentrated skim milk: importance of soluble minerals in the changes in viscosity during storage", J. Diary Sci., 2003, vol. 86, pp. 3813-3821.
Diary Processing Handbook, 1995, Chapter 20, Tetra Pak Processing Systems AB.
Karlsson et al., "Relationship between physical properties of casein micelles and rheology of skim milk concentrate", J. Dairy Sci., 2005, vol. 88, pp. 3784-3797.
Novartis Nutrition Pocket Guide, Resource Optisource High Protein Drink, 2004.
Peng et al., "Effect of fortification with various types of milk proteins on the rheological properties and permeability of nonfat set yogurt", Journal of Food Science, 2009, vol. 74, No. 9, C666-C673.
Product Brochure: Fresubin 2kcal Fibre Drink, Jan. 2009.
Smith, "Dried Dairy Ingredients", Wisconsin Center for Dairy Research, May 15, 2008, pp. 1-59.
Walstra et al., Dairy Science and Technology, 2006, 2nd Edition, Chapter 2.2, pp. 26-37.

* cited by examiner

*Primary Examiner* — Marcela M Cordero Garcia
*Assistant Examiner* — Catherine Mader
(74) *Attorney, Agent, or Firm* — Foley & Lardner LLP; Sunit Talapatra

(57) ABSTRACT

Heat-treated liquid enteral nutritional composition with a low monovalent metal ion content are provided that contain micellar casein and optionally caseinate, and in which the total amount of monovalent metal ions is less than 25 mg/g of protein. Also, heat-treated liquid enteral nutritional compositions are disclosed comprising 10 to 20 g of protein per 100 ml of the composition, in which all or a major part of said protein comprises micellar casein. Also, a method is disclosed for producing the composition according to the invention, comprising a step wherein an aqueous protein solution in which all or a major part of said protein comprises micellar casein, is subjected to an evaporation step.

22 Claims, No Drawings

LIQUID ENTERAL NUTRITIONAL COMPOSITION WITH A LOW MONOVALENT METAL ION CONTENT

FIELD OF THE INVENTION

The present invention is in the field of liquid enteral nutritional compositions.

BACKGROUND OF THE INVENTION

The present invention relates in general to a shelf-stable liquid enteral composition for providing nutrition, either as a supplement, or as a complete nutrition, comprising a high amount of micellar casein.

Some patients need nutrition, either as a supplement, or as a complete nutrition, in the smallest volume of liquid. Special care must be taken to their protein levels.

These patients can be cachectic patients or persons suffering from end-stage AIDS, cancer or cancer treatment, severe pulmonary diseases like COPD (chronic obstructive pulmonary disease), tuberculosis and other infection diseases or persons that experienced severe surgery or trauma like burns. Furthermore, persons suffering from disorders in the throat or mouth such as oesophageal cancer or stomatitis and persons having problems with swallowing like dysphagic persons, require special liquid, low-volume nutrition. Also, persons just suffering from reduced appetite or loss of taste, will benefit from low-volume, preferably liquid, food.

These patients can also be elderly persons, in particular frail elderly and elderly at risk of becoming frail. In this regard, although an elderly person's energy needs may be reduced, their ability to consume products may also be diminished. For example, they may have difficulty consuming a product due to, e.g., swallowing difficulties, or due the too large amount of product they need to consume to meet the daily intake of nutrients. Hence, compliance is not optimal, and often, the intake is suboptimal, leading to suboptimal nourishment, and in the end, to malnutrition.

The aforementioned groups of patients may be extremely sensitive to food consistency and to the organoleptic properties of the product such as, for instance viscosity, mouth feel, taste, smell and colour. Also, patients such as cachectic patients, typically suffer from extreme weakness which often prevents them from sitting in a vertical position and from drinking food from a carton or even to suck it from a straw. These patients benefit well from liquid low-volume enteral compositions with a high content of nutrients, in particular proteins.

However, increasing calories and/or proteins in a nutritional liquid composition may increase the overall viscosity of the composition. This can make the liquid nutritional composition difficult to consume or administer, and can also diminish the taste of the nutritional composition. Furthermore, technical difficulties exist in producing a stable, in particular a shelf-stable nutritional liquid composition having a high content of proteins.

Therefore, the problem underlying the present invention is to provide a shelf-stable liquid enteral composition for providing nutrition, either as a supplement, or as a complete nutrition, comprising a high content of an intact protein, as major protein source, in the smallest volume of liquid, and which supports nutrition and well-being in the different patient groups mentioned above, in particular to an elderly person or an ill patient.

Major technical difficulties exists in producing such a shelf-stable liquid enteral nutritional composition with a high content of proteins, in particular intact proteins.

For example, increasing the amount of proteins leads to precipitation and sedimentation of proteins and other ingredients, such as lipids and digestible carbohydrates, which imparts nutrient intake.

Concentrating liquids also increases the chance of undesired interactions between ingredients which reduces stability, especially during heating and long-term storage. Shelf-stable is defined as having a stability of more than 6 months on the shelf under normal storage conditions, i.e. at an ambient temperature of between 18 and 25° C., and at a standard atmospheric pressure.

Furthermore, increasing the protein content in a nutritional liquid composition may increase the overall viscosity of the composition. This can make the liquid nutritional composition difficult to consume or administer, and can also diminish the taste of the nutritional composition. These phenomena often follow non-linear kinetics and the problems quickly increase in magnitude when the concentration of ingredients is increased above 28 weight %. Therefore, many of the commercial shelf-stable liquid products that are currently available have intact protein levels below about 9 g per 100 ml of product.

A known solution to the problem how to increase the protein content to a higher level without imparting viscosity is replacing part of the total protein by peptides or free amino acids. However, this seriously decreases taste appreciation and therefore voluntary intake of the nutritional composition by the patient group.

On the other hand, many concentrates like condensed milks suffer from an incomplete nutrient profile, too high lactose levels, sticky mouth-feel, high viscosity, extreme sweetness and a high osmotic value, which is not appreciated by the consumer and increases rapidly feelings of fullness and satiety after consumption. This makes that the urge to consume more volume deteriorates rapidly once a small amount of the product has been consumed.

PRIOR ART

U.S. Pat. No. 5,683,984 (Nestec S. A.) and the corresponding EP patent 0 686 396 B1 (Nestec S. A., 13 Dec. 1995) teach to replace all of the caseinate in a medium energy nutritional formulation (1 kcal/ml) by native micellar casein to obtain a formulation essentially containing native micellar casein with a low viscosity and a thermal stability to withstand sterilization. To this end, it discloses the use of a retentate that is an ingredient which is combined with other ingredients such as fats and carbohydrates to form an enteral composition. The nutritional (and sterilized) composition contains a maximum of about 7.6% of native micellar casein and a total monovalent metal ion content (Na+K) of about 28 mg per g of protein (composition A). However, the latter document does not teach to replace only part of the caseinate by native micellar casein in a high energy, high protein nutritional formulation and the problems that would arise in doing so, nor does it teach the poor shelf and heat stability upon sterilization.

WO 2008/041219 (Kerry Group Services International Limited, 10 Apr. 2008) discloses a dry milk protein composition comprising at least 12.5 weight % of a slow digesting milk protein, in particular micellar casein. The milk protein composition is first provided in the form of a powder, which is then used into in beverages, desserts, confectionary, baked or dairy products, without pasteurisation or sterilisation. A liquid high protein shake containing 11.4% Ultra Bio-M™ (about 8 weight % of protein) is exemplified. A high protein content of more than 10 weight % and the associated problems were not addressed.

XP002516238 (internet citation "*Muscle Milk, Nature's Ultimate Growth Formula*" 23 Jul. 2003) discloses a powder to be mixed with water, comprising a.o. micellar alpha and beta caseins, caseinates, whey, sugars and fat. It does not teach a shelf-stable liquid enteral composition that has been subjected to heat treatment. The role of monovalent metal ions is unnoticed.

WO 98/18350 (Unilever, 7 May, 1998) describes ice confection having an aqueous phase and a fat phase, wherein at least 1 weight % and preferably up to 5 weight % of micellar casein is present in the aqueous phase. A product which is perceived to be thicker is strived for. The test results presented in Figure 2 and Example 8 show fat-free compositions containing low micellar casein levels up to 6.5 weight %. The document is silent on monovalent metal ion concentrations.

WO 2009/072886 (NV Nutricia, 11 Jun. 2009) discloses liquid high-protein enteral compositions, but is silent on the role of monovalent metal ions.

EP 1 563 741 A1 (Campina, 17 Aug. 2005) discloses a skimmed milk product for consumption. It attempts to replace at least part of the milk fat and to compensate for a loss of flavour and mouthfeel associated with milk fat. The micellar casein content is low, typically between 3.1 and 3.4 weight % of the total skimmed-milk product.

SUMMARY OF THE INVENTION

The present invention provides a liquid enteral nutritional composition with a high protein content, designed to meet the nutritional needs of persons in need thereof, in particular elderly and patients with certain disease states. In one aspect, the present invention provides a liquid enteral nutritional composition comprising to a large extent micellar casein, designed to meet the nutritional needs of persons in need thereof, in particular elderly and patients with certain disease states. The composition provides an increased amount of protein per unit volume while providing a sufficiently low viscosity to allow the composition to be easily consumed orally or be administered by tube.

Surprisingly, the inventors have now found that such a composition can be provided mainly based on micellar casein, when the total amount of monovalent metal ions, in particular the sum of sodium and potassium (Na+K) is low, preferably less than 25 mg/g of total protein in the composition. At higher monovalent metal ion concentrations the viscosity starts to rise steeply, as it is demonstrated in and around Table 2 further below. At higher concentrations, undesirably high viscosities of 300 mPas and beyond are readily obtained. Such high viscosities are disadvantageous both in manufacturing and in the consumer's appreciation of the product. In addition, surprisingly, the overall appreciation of the composition is improved (according to a QDA panel experiment testing smell, taste, mouthfeel (sticky and slimy), and aftertaste) compared to equivalent compositions with a total amount of monovalent metal ions of more than 25 mg/g of protein.

To this end, in a first aspect of the present invention, a liquid enteral nutritional composition is provided comprising 10 to 20 g of protein per 100 ml of the composition, in which all or a major part of said protein comprises micellar casein, and in which the total amount of monovalent metal ions, more in particular the sum of sodium and potassium (Na+K) is less than 25 mg/g of protein, preferably less than 20 mg/g of protein, more preferably less than 15 mg/g of protein, most preferably less than 10 mg/g of protein.

In a particularly preferred embodiment, the amount of potassium is less than 25 mg/g of protein, preferably less than 20 mg/g of protein, more preferably less than 15 mg/g of protein, more preferably less than 10 mg/g of protein, most preferably less than 5 mg/g of protein.

In a particularly preferred embodiment, the amount of sodium is less than 25 mg/g of protein, preferably less than 20 mg/g of protein, more preferably less than 15 mg/g of protein, more preferably less than 10 mg/g of protein, most preferably less than 5 mg/g of protein.

In particular, a liquid enteral nutritional composition is provided in which all or a major part of said protein comprises micellar casein, providing 10% to 100% of the total energy content of the composition, said protein comprising to a large extent micellar casein.

Micellar casein, sometimes also referred to as "native" micellar casein, refers to casein in the form of micelles, which is the native form of casein in milk. It is a high quality milk protein and naturally occurring in milk in a concentration of about 2.6 g/100 ml (Dairy Science and Technology, Walstra et al., CRC Press, 2006). It is concentrated by a process that does not, or does not substantially denature the casein proteins and it is marketed as Micellar Casein Isolate (MCI). Fresh skim milk is subjected to a microfiltration process, in much the same process used to concentrate whey protein, to produce a pure, substantially undenatured milk protein with its native structure. The resulting material contains between 90% and 95%, preferably more than 95% by weight of micellar casein on dry matter, the rest mainly being whey protein and other non-protein nitrogen and other constituents, such as lactose and inorganic salts, in particular calcium phosphate. The casein micelles generally have a hydrodynamic radius of 40 to 400 nm, a molecular weight of $10^6$ to $10^9$ Dalton and a calcium:phosphorous weight ratio of 1.4 to 2.4, the calcium-content being very high, in the order of about 25 g/kg protein. It has an intrinsic low viscosity and a liquid composition comprising said MCI is therefore easy to drink. The amount of monovalent metal ions, in particular Na and K, is very low, typically about 2 g/kg protein. It is emphasized that the role of these monovalent ions in MCI is not recognized in the art, and that the prior art thus lacks the incentive and the means to control the concentration of monovalent ions in the manufacture of a nutritional composition comprising high amounts of MCI, especially amounts above 10 g/100 ml.

In contrast, casein, as it is used in the context of this invention refers to the curd form of casein, having lost its native micellar structure. It is bound to a metal, such as sodium, potassium, calcium and magnesium.

Within the context of this invention, it is understood that micellar casein may also be provided by other milk protein sources, such as, for instance, sources with essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk. The micellar casein may also be provided in liquid form via an ultrafiltrate or microfiltrate.

A problem associated with the use of micellar casein isolate in the production of liquid enteral nutritional compositions with a high protein content is the dissolution of the large amounts of protein powders in the small quantity of water. A viscous intermediate state is produced which is difficult to handle and to process. Especially in highly protein-dense formulations the viscosity may be too high to pump, heat, cool or homogenize the solution, all processes which are necessary to obtain the final product. It is obvious that only the final heat-treated (by pasteurisation or sterilisation) product needs to have a low viscosity such that it may be consumed orally or by tube.

A further problem associated with the use of micellar casein in the production of liquid enteral nutritional compositions with a high protein content and further containing acids, in particular citric acid, is the formation of calcium-acid complexes, such as calcium citrate. In particular citric acid is added to the composition to adjust the pH and also to adjust Ca-ion activity. A certain Ca-ion activity is beneficial to maintain a desired viscosity of the composition during processing of the composition, in particular during heat-processing of the composition, e.g. during pasteurisation and/or sterilisation. Calcium, originating from the micellar casein, tends to react with acid, in particular the citric acid, thus forming calcium citrate crystals, which precipitate when the acidity of the composition increases over time (pH lowering), giving rise to a poor shelf stability. Already at a pH of 6.9, the formation of Ca-citrate crystals is progressing. On the other hand, a certain Ca-ion activity is beneficial to maintain a desired viscosity of the composition during processing of the composition, in particular during heat-processing of the composition, e.g. during pasteurisation and/or sterilisation. In particular, a certain Ca-ion activity is beneficial to prevent a viscosity increase during heating. Thus, besides shelf stability, it is a problem to arrive at a proper viscosity when using micellar casein.

Furthermore, it was observed by the inventors that the amount of monovalent metal ions seriously influences the viscosity when heat-treating the product (i.e., by sterilization or pasteurization), in the sense that a high monovalent metal ions content leads to unacceptable high viscosities.

Without being bound by theory, it is believed that a high concentration of these monovalent metal ions makes the casein micelle more voluminous. If the amounts are not low enough, the final heat-treated (i.e. sterilized or pasteurized) product becomes viscous, sticky or aggregated.

These problems associated with heat treatment have now surprisingly been solved by the inventors using a specific method, in a particular embodiment for a composition comprising micellar casein and optionally caseinate. As implied in foregoing and unless otherwise indicated, the composition according to the invention is a heat-treated composition, i.e. a composition which as been (heat) sterilized and/or pasteurized, preferably (heat) sterilized. Also implied, the terminology "heat-treated composition" is not to be mistaken for any heat treatment steps such as evaporation steps which may or may not have been applied to one or more of its ingredients, but it refers to a product comprising protein(s), fat(s) and carbohydrate(s) which has been subjected to a heat treatment per se.

In a further aspect, the present invention concerns a method of producing a liquid enteral nutritional composition comprising 10 to 20 g of protein per 100 ml of the composition, in which all or a major part of said protein comprises micellar casein, and in which the total amount of monovalent metal ions, in particular the sum of sodium and potassium, is less than 25 mg/g of protein.

In a further aspect, the present invention concerns a method of producing a liquid enteral nutritional composition comprising 10 to 20 g of protein per 100 ml of the composition, in which all or a major part of said protein comprises micellar casein, and in which the total amount of monovalent metal ions, in particular the sum of sodium and potassium, is less than 25 mg/g of protein, wherein liquid enteral nutritional composition is subjected to an evaporation step.

In a further aspect, the present invention concerns a method of providing nutrition to a person in need thereof, comprising the steps of administering to said person the nutritional composition according to the present invention.

In a further aspect, the present invention concerns the use of micellar casein and optionally caseinate in the manufacture of a liquid nutritional composition according to the present invention for providing nutrition to a person.

In the context of this invention, the term "at least" also includes the starting point of the open range. For example, an amount of "at least 95 weight %" means any amount equal to 95 weight % or above.

In the context of this invention, enteral means orally or by tube.

In the context of this invention, the % of total energy is also abbreviated as En %; En % is thus short for energy percentage and represents the relative amount that a constituent contributes to the total caloric value of the composition.

In the context of this invention, the term "about" indicates that a certain deviation is allowed from a cited value, the magnitude thereof being determined by inter alia the accuracy of the determination method. Typically, such a deviation is 10%.

In the context of this invention, "non-hydrolysed" proteins is equivalent to "intact" proteins, meaning that the proteins have not, or not substantially, been subjected to a hydrolysis process. However, minor amounts of hydrolysed proteins may be present in the source of non-hydrolysed proteins, or may be added to the formulation, such as additional amino acids, such as for example branched chain amino acids, for example leucine, isoleucine, valine and the like. In this context, "minor" should be understood as an amount of about 10 weight % or less, based on total protein.

In the context of this invention, intact milk protein is defined as a milk protein in its native state originating from milk.

In the context of this invention, it is understood that "liquid" refers to a water-based composition, such as a solution or a suspension, having a viscosity of 200 mPa·s or less, as determined at 20° C. in a rotational rheometer at a shear rate of 100 s$^{-1}$. A value of about 200 mPa·s is herewith defined as an empirical upper viscosity limit, above which a liquid system has an unacceptably high viscosity to be readily drinkable. It is preferred to provide a composition having a viscosity of less than 200 mPa·s, more preferably 150 mPa·s or less, more preferably 120 mPa·s or less, more preferably 100 mPa·s or less, more preferably 80 mPa·s or less, most preferably 50 mPa·s or less.

In the context of this application, "major" is to be interpreted as at least 70 weight %, more preferably at least 80 weight %, most preferably at least 90 weight %.

The invention will now be further elucidated by describing the preferred embodiments of the present invention in more detail.

DETAILED DESCRIPTION OF THE INVENTION

Protein

According to one embodiment of the present invention, a liquid enteral nutritional composition is provided comprising 10 to 20 g of protein per 100 ml of the composition, preferably at least 11, 12, 13, 14, 15, 16, 17, 18 or 19 g and at most 20 g of protein per 100 ml of the composition, preferably 11 to 18 g/100 ml, more preferably 12 to 18 g/100 ml, and most preferably 14 to 18 g/100 ml of the composition, in which all or a major part of said protein comprises micellar casein.

According to another embodiment of the present invention, the liquid enteral nutritional composition of the invention comprises a total amount of monovalent metal ions less than 25 mg/g of protein, preferably less than 24, 23, 22, 21, 20, 19, 18, 17, 16, 15, 14, 13, 12, 11, 10, 9, 8, 7, 6 or 5 mg/g of protein.

According to another embodiment of the present invention, the liquid enteral nutritional composition of the invention comprises a total amount of monovalent metal ions ranging between 5 and 25 mg/g of protein, preferably between any of the amounts 24, 23, 22, 21, 20, 19, 18, 17, 16, 15, 14, 13, 12, 11, 10, 9, 8, 7, 6 or 5 mg/g of protein.

The concentrations of monovalent metal ions in the above paragraphs are based on the total amount of protein, preferably on the total amount of micellar casein and caseinate, more preferably based on the total amount of micellar casein in the liquid enteral nutritional composition of the invention.

According to another embodiment of the present invention, the liquid enteral nutritional composition of the invention comprises optionally at most 30 weight % of caseinate, based on the total weight of the protein.

According to another embodiment of the present invention, the protein provides 10% to 100%, preferably 20% to 80%, more preferably 30% to 70%, most preferably 30% to 60% of the total energy content of the composition. The high levels of protein are beneficial for patients who may not be physically capable of receiving a large volume, for example, fluid restricted patients. Such patients can be given a reduced level of fluid while still receiving a required amount of nutritional support per day. The composition may be used as a complete nutrition, in addition to or as a replacement for a normal meal consumption. The composition may also be used as a supplement, in addition to normal meal consumption, when the uptake of fats and carbohydrates is of less concern.

According to another embodiment of the present invention, the composition has an energy density of at least 0.40 kcal/ml, more preferably at least 1.0 kcal/ml, particularly at least 1.5 kcal/ml of composition.

According to another embodiment of the present invention, the composition has an energy density of less than 2.0 kcal/ml. Although the composition has a high energy density, it also has a sufficiently low viscosity to allow it to be consumed by persons that may have difficulty swallowing products or those that are tube fed.

In one embodiment of the present invention, the amount of micellar casein in the liquid nutritional composition according to the invention is at least 70 weight %, preferably at least 80 weight %, more preferably at least 90 weight %, more preferably at least 95 weight % and at most 100 weight % of the total protein present in the liquid nutritional composition.

As aforementioned, the composition of the present invention should not contain large amounts of proteins other than micellar casein and optionally at most 30 weight % of caseinate. In a further embodiment of the present invention, the composition may comprise up to about 15 weight % of whey, preferably less than or equal to 10 weight % of whey, more preferably, less than or equal to 5 weight % of whey of the total protein present in the liquid nutritional composition.

In one embodiment of the present invention, divalent metal ion-caseinate, such as Ca-caseinate, Mg-caseinate or any mixture or combinations thereof are used as the source of caseinate. Preferably, monovalent metal ion-caseinate, such as K-caseinate or Na-caseinate is not used, as it adds to the amount of monovalent metal ions such as K and Na in the nutritional composition, which is limited to 25 mg/g of protein. Furthermore, large quantities of Ca-caseinate should not be used as the micellar casein already contains a sufficient amount of calcium, and the formation of further calcium crystals should be avoided.

In one embodiment of the present invention, the weight ratio of micellar casein to caseinate ranges from about 100:0 to about 70:30. Preferably, the weight ratio of micellar casein to caseinate ranges from about 80:20 to about 100:0.

The composition according to the invention is designed to either supplement a person's diet or to provide complete nutritional support. Hence, the composition according to the invention may further comprise at least fat and/or carbohydrate and/or a source of vitamins, minerals, trace elements and/or a source of indigestible carbohydrates. Preferably, the composition according the invention is a nutritionally complete composition.

Fat

In one embodiment the present liquid enteral nutritional composition further comprises fat. The amount of fat may range between 5 and 95%, preferably between 10 and 70%, more preferably between 20 and 40%, relative to the total energy content of the composition.

With regard to the type of fat, a wide choice is possible, as long as the fat is of food quality.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil and/or sunflower oil.

The fat may include a source of medium chain fatty acids, such as medium chain triglycerides (MCT, mainly 8 to 10 carbon atoms long), a source of long chain fatty acids, such as long chain triglycerides (LCT) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

In one specific embodiment, the fat comprises 30 to 60 weight % of animal, algal or fungal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil is used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexaenoic acid (DHA), i.e. less than 6 weight %, preferably less than 4 weight % based on total fat. Marine oils containing DHA are preferably present in the composition according to the invention in an amount lower than 25 weight %, preferably lower than 15 weight % based on total fat. On the other hand, inclusion of eicosapentaenoic acid (EPA) is highly desirable for obtaining the maximum health effect. Therefore, in another embodiment, the amount of EPA may range between 4 weight % and 15 weight %, more preferably between 8 weight % and 13 weight % based on total fat. The weight ratio EPA:DHA is advantageously at least 6:4, for example between 2:1 and 10:1. In yet another embodiment, the amount of EPA is very low, such as 0.1 to 1 weight %, preferably 0.3 weight % or 0.6 weight %, based on total fat.

Also, the liquid nutritional composition according to the invention may beneficially comprise an emulsifier. Commonly known emulsifiers may be used and generally the emulsifier contributes to the energy content of the fat in said composition.

Digestible Carbohydrate

In one embodiment of the present invention, the liquid nutritional composition according to the invention further comprises a digestible carbohydrate. Preferably, the digestible carbohydrate provides between 30 to 60% of the total energy content of the composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and polysaccharides.

The composition of the digestible carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the digestible carbohydrates between 1.5 and 6, preferably between 1.8 and 4. In order to avoid excessive sweetness, the total level of sucrose and fructose is preferably less than 60%, more preferably less than 52%, more preferably less than 40% of the weight of the carbohydrate, especially of the digestible carbohydrate. Long-chain digestible carbohydrates such as starch, starch fractions and mild starch hydrolysates (DE≥6, DE<20), may also be present, preferably in an amount of less than 25 weight %, especially less than 15 weight % of the digestible carbohydrate, and less than 6 g/100 ml, preferably less than 4 g/100 ml of the total liquid enteral composition according to the invention.

In one embodiment of the present invention, the digestible carbohydrate includes maltodextrose with a high DE (dextrose equivalent). In one embodiment the digestible carbohydrate includes maltodextrose with a DE of >10, preferably a DE of >20, more preferably >30 or even >40, such as a DE of about 47. In one embodiment of the present invention, the digestible carbohydrate includes maltodextrose with a DE>10 and sucrose.

Surprisingly, the use of maltodextrose leads to few or no Maillard reaction products upon heating. Without being bound to any explanation, this effect might be attributed to the fact that the compact micellar structure of the micellar casein offers few lysine reaction sites for a Maillard reaction. In one embodiment of the present invention, the digestible carbohydrate includes maltodextrose with a high DE in an amount of at least 35 weight %, preferably at least 50 weight %, preferably at least 65 weight %, preferably at least 90 weight % of the total weight of digestible carbohydrate. In one embodiment of the present invention, the digestible carbohydrate includes maltodextrose with a low DE of 2 to 20. In one embodiment of the present invention, the digestible carbohydrate includes maltodextrose with a low DE of 2 to 10, preferably with a low DE of about 2. In one embodiment of the present invention, the digestible carbohydrate includes maltodextrose with a low DE in an amount of less than 35 weight %, preferably less than 20 weight %, preferably less than 10 weight % of the digestible carbohydrate. Maltodextrose with a low DE may also be referred to as maltodextrine. In another embodiment of the present invention, the digestible carbohydrate includes maltodextrose with a high DE, preferably a DE of >20, preferably >30 or even >40, most preferably a DE of about 47 in combination with maltodextrose with a low DE, preferably a low DE of 2 to 20, more preferably a low DE of 2 to 10, most preferably with a low DE of about 2. As is known, maltodextrose with a low DE, such as of about 2, gives rise to a high viscosity. Maltodextrose with a high DE, such as of about 47 gives rise to a low viscosity, but is very sweet. The combination of both maltodextroses optimizes the balance between sweetness and viscosity. In one embodiment of the present invention, the digestible carbohydrate includes at least 65 weight %, preferably at least 90 weight %, based on total weight of digestible carbohydrate of maltodextrose with a DE>40, preferably with a DE of about 47 and 0 to 10 weight % of maltodextrose with a DE 2 to 10, preferably with a DE of about 2.

In another embodiment of the present invention, the digestible carbohydrate includes trehalose. As was indicated, it is one of the main objects of the invention to provide a nutritional composition with a low viscosity. Sucrose is very well suited for such purpose, but gives rise to very sweet compositions, which are in general disliked by the consumer. Maltodextrose with a low DE, such as of about 2, does not suffer from the latter drawback, but gives rise to a high viscosity. Maltodextrose with a high DE, such as of about 47 gives rise to a low viscosity, but is again very sweet, and gives further rise to the undesired Maillard reactions. Trehalose is a preferred choice of carbohydrate, as it gives rise to a low viscosity, no undesired Maillard reactions and it has a sweetness about half of that of sucrose. In one embodiment of the present invention, the digestible carbohydrate includes trehalose in an amount of 20% to 60% of the weight of the carbohydrate, in an amount of 20% to 45%, more preferably in an amount of 25% to 45% of the weight of the digestible carbohydrate.

Vitamins, Minerals and Trace Elements

The composition according to the invention may contain a variety of vitamins, minerals and trace elements.

In one embodiment of the present invention, the composition according to the invention provides all necessary vitamins, most of the minerals and trace elements. For example, the composition according to the invention preferably provides 6 mg of zinc per 100 ml of the composition which is beneficial for tissue repair in a healing patient. Preferably, the composition according to the invention (also) provides 25 mg of vitamin C per 100 ml of the composition to aid patients with more severe healing requirements. Further, preferably, the composition according to the invention (also) provides 2.25 mg iron per 100 ml of the composition. Iron is beneficial in maintaining bodily fluids as well as circulatory system functions in an elderly patient.

The invention implicates that a composition according to the present invention may contain sodium and/or potassium levels outside FSMP (Foods for Special Medical Purposes) legislation levels.

In another embodiment of the present invention, the amount of divalent metal ions ranges between 170 mg/100 ml and 600 mg/100 ml and preferably between 200 mg/100 ml and 500 mg/100 ml. Preferably, the amount of calcium ranges between 170 mg/100 ml and 600 mg/100 ml and more preferably between 200 mg/100 ml and 500 mg/100 ml. Preferably, the amount of magnesium ranges between 13 mg/100 ml and 100 mg/100 ml and more preferably between 20 mg/100 ml and 70 mg/100 ml. The phosphorus content can be above 10 mg per g of protein, with a calcium to phosphorus weight ratio between 1.0 and 2.0, preferably between 1.1 and 1.7. Carnitin may advantageously be present in an amount of 8 mg/100 ml to 1000 mg/100 ml, preferably 10 mg/100 ml to 100 mg/100 ml of composition; it may have the form of carnitin, alkyl carnitin, acyl carnation or mixtures thereof. Organic acids are preferably present at a level of between 0.1 g/100 ml to 0.6 g/100 ml, especially 0.25 g/100 ml to 0.5 g/100 ml. These acids include short fatty acids such as acetic acid, hydroxy acids such as lactic acid, gluconic acid, and preferably polyvalent hydroxy acids, such as malic acid and citric acid. In one embodiment of the present invention, the present composition also comprises citric acid.

Non-Digestible Carbohydrates

The liquid enteral nutritional composition according to the invention may optionally be fortified with non-digestible carbohydrates (dietary fibres) such as fructo-oligosaccharides or inulin. In an embodiment of the present invention, the composition according to the invention comprises 0.5 g/100 ml to 6 g/100 ml of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylooligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, and/or below 0.6 g/100 ml. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 ml. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides, which may also contain a small amount of higher saccharides (e.g. with a DP of 11 to 20). Such oligosaccharides preferably comprise 50 weight % to 90 weight % of the fibre fraction, or 0.5 g/100 ml to 3 g/100 ml of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety. More in particular, the acid oligosaccharide has a degree of polymerization (DP) between 1 and 5000, preferably between 1 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%.

Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, β-D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclo dextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxohexylose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-gluco-pyranose), synthetic galactooligosaccharide (neogalactobiose, isogalactobiose, galsucrose, isolactose I, II and III), fructans—Levan-type (β-D-(2→6)-fructofuranosyl)$_n$α-D-glucopyranoside), fructans—Inulin-type (β-D-((2→1)-fructofuranosyl)$_n$α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosaccharides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin, alginate, and mixtures thereof; and a neutral oligosaccharide, selected from the group of fructans, fructooligosaccharides, indigestible dextrins, galactooligosaccharides including transgalacto-oligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect.

Preferably the composition according to the invention comprises:
  an acid oligosaccharides as defined above;
  a galactose-based neutral oligosaccharide (of which more than 50% of the monose units are galactose units), preferably selected from the group consisting of galactooligosaccharide and transgalactooligosaccharide; and
  a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

The mixture of acid- and neutral oligosaccharides is preferably administered in an amount of between 10 mg and 100 gram per day, preferably between 100 mg and 25 grams per day, even more preferably between 0.5 and 20 gram per day.

Viscosity and Osmolarity

In the context of this invention, the viscosity is measured in a rotational rheometer using a cone-plate geometry at 20° C. at a shear rate of 100 s$^{-1}$.

In one embodiment of the present invention, the viscosity of the liquid enteral nutritional composition is less than 200 mPa·s, more preferably less than 150 mPa·s, more preferably less than 120 mPa·s, more preferably less than 100 mPa·s, more preferably less than 80 mPa·s, and most preferably 50 mPa·s.

A low viscosity is ideal for orally administering the liquid enteral nutritional composition according to the invention because a person may easily consume a serving having a low viscosity such as that displayed by the present invention. This is also ideal for unit dosages that are tube fed.

In one embodiment of the present invention, the osmolarity of the composition is preferably lower than 1200 mOsm/l, more preferably lower than 900 mOsm/l, more preferably lower than 800 mOsm/l, and most preferable lower than 700 mOsm/l.

In one embodiment of the present invention, the density of the composition ranges between 1.05 g/ml and 1.20 g/ml, especially between 1.10 g/ml and 1.18 g/ml.

Dosage Unit

The liquid enteral nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units, e.g. from 4 (250 ml/unit) to 40 (20 ml/unit) per day for an energy supply of 2000 kcal/day using a liquid enteral nutritional composition according to the invention of 2.0 kcal/ml.

The liquid enteral nutritional composition can also be a food supplement, for example to be used in addition to a non-medical food. Preferably as a supplement, the liquid enteral nutritional composition contains per daily dosage less than 1500 kcal, in particular as a supplement, the liquid enteral nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using a liquid enteral nutritional composition according to the invention of 2.0 kcal/ml.

In one embodiment of the present invention, a unit dosage comprises any amount of the liquid enteral nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using a liquid enteral nutritional composition according to the invention of 2.0 kcal/ml. Alternatively a person receiving 125 ml unit dosages can be given 4 or 5 or 6 or 7 or 8 unit dosages per day to provide nutritional support using a liquid enteral nutritional composition according to the invention of 2.0 kcal/ml. Such small dosage units are preferred because of better compliance.

In one embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

In one embodiment of the present invention, the composition according to the invention (optionally heat-treated) may be used as a basis for the manufacturing of a semi-solid nutritional composition, such as a crème, a pudding, a custard, a soup, an ice cream, or a gelly. To this end, the composition according to the invention (optionally heat-treated) is processed to convert the low viscosity composition according to the invention into a more sold or viscous one, e.g. by adding thickeners or gelling agents and further process the mixture into the final product, e.g. by subjecting it to a heat-treatment. Thickeners and/or gelling agents can also be present in the formulation from a more earlier stage of the process, or even dissolved together with the nutrients at the beginning of the process.

Hence, according to one embodiment, the invention is related to a heat-treated semi-solid enteral nutritional composition comprising 10 to 20 g of protein per 100 ml of the composition, in which at least 70 weight % of said protein comprises micellar casein, and in which the total amount of monovalent metal ions is less than 25 mg/g of protein, obtainable by combining a thickener or gelling agent with an optionally heat-treated liquid enteral nutritional composition according to the invention.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

Preparation

The liquid enteral nutritional composition according to the invention may be prepared by as indicated in the Examples.

The liquid enteral nutritional composition according to the invention may be prepared by an inventive process comprising a step wherein an aqueous protein solution in which all or a major part of said protein comprises micellar casein, is subjected to an evaporation step.

Firstly, a liquid protein composition is prepared. This may be done by sequentially or simultaneously dissolving micellar casein in powder form (such as MCI) and optionally caseinate in powder form in water. In order to obtain a low-viscosity protein solution which can be processed further, the protein ingredients are dissolved in an excess of water, typically 150 weight % or volume % of what is required for the final composition. Without this excess of water, the protein solution is too thick for homogenization and pasteurisation.

Furthermore, if the liquid enteral nutritional composition is to contain further components, such as carbohydrates, fat and vitamins, a nutritional product may be prepared by subsequently adding the carbohydrates to the protein composition, followed by optionally adding the water-soluble vitamins and other components in one or two stages, mixing, adding the fat, including fat-soluble vitamins, homogenizing, and subjecting the resulting solution to a pasteurization step. The pH may be adjusted. The intermediate enteral nutritional composition is now subsequently concentrated to the desired dry matter concentration by an evaporation step to get rid of the excess of water. Evaporation may be performed at atmospheric pressure at a temperature of typically above 60° C., or preferably under vacuum at a temperature of typically 60° C. A higher viscosity may be obtained by this evaporation step. Surprisingly, the viscosity of the resulting solution is still low enough to have a sufficient heat transfer in the product to optimally subject the product to the final heat treatment necessary for providing the product with a long microbial shelf life (sterilization). In this respect, it is noted that the acidity of the composition is very important during the heat-treatment. The pH should be between about 6.2 and 7.2 for the pasteurisation and sterilisation. Typical pasteurisation times are 30 sec at 85° C. Typical sterilisation times are 4 minutes at 124° C. Surprisingly, the final heat treatment (sterilisation) decreases the viscosity of the treated composition such that a microbial stable product is obtained with a much lower viscosity than before the sterilisation. Without being bound to any explanation, it is believed that during the extensive final heat treatment (sterilisation), restructuring of the micellar casein into a more compact structure results in a lowering of the viscosity. Surprisingly, the product viscosity did not change substantially during storage over longer periods of time, which provides the product with a long shelf life.

Surprisingly, liquid sterilized products with high protein concentrations could be prepared.

The invention therefore relates in particular to a method for preparing the compositions of the invention, comprising a step wherein an aqueous protein solution, obtained by dissolving a micellar casein in powder form, and optionally micellar casein in powder form, is subjected to an evaporation step.

In the manufacturing of the composition according to the invention only additives can be used which do not increase the monovalent metal ion content above 25 mg/g of protein. For example, the use of potassium citrate for adjusting the pH, or the use of NaCl is limited or avoided.

As can be understood by the reader, the invention is not restricted to the above dissolution order, ingredients, processes or heating steps.

Effectivity

The present invention also concerns a method of providing nutrition to a person in need thereof, comprising the steps of administering to said person the nutritional composition according to the present invention. Said person may be an elderly person, a person that is in a disease state, a person that is recovering from a disease state, or a person that is malnourished.

In this respect, it is submitted that in the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

In a further aspect, the present invention also concerns the simultaneous or sequential use of micellar casein and optionally caseinate in the manufacture of a liquid nutritional composition according to the present invention in which the total amount of monovalent metal ions, in particular the sum of sodium and potassium, is less than 25 mg/g of protein for providing enteral nutrition to a person in need thereof. In one particular embodiment of the present invention, said composition provides 10 to 20 g of protein per 100 ml of composition, in which all or a major part of said protein comprises micellar casein. In another particular embodiment of the present invention, said protein provides 10% to 100% of the total energy content of the composition.

In one embodiment, the present invention concerns a liquid enteral nutritional composition according to the invention, comprising about 14 to 16 g of protein per 100 ml of the composition, comprising micellar casein and optionally caseinate with a weight ratio of micellar casein to caseinate of about 80:20 to 100:0, said protein providing 20 to 40% of the total energy content of the composition, said composition having an energy density of about 1.0 to 3.5 kcal/ml.

In one embodiment, the present invention concerns a liquid enteral nutritional composition according to claim 1, comprising:
a) about 15 g of protein per 100 ml of the composition, comprising micellar casein and optionally caseinate with a weight ratio of micellar casein to caseinate of about 80:20 to 100:0, said protein providing about 25% of the total energy content of the composition;
b) fat providing about 35% of the total energy content of the composition;
c) carbohydrate providing about 40% of the total energy content of the composition, said composition having an energy density of about 2.4 kcal/ml.

Examples

The following compositions according to the invention have been prepared as follows.

Preparation A

Six batches of 18 l were prepared. Sucrose (about 2.1 kg) was dissolved in tap water (about 11 kg) of about 60° C. Next, the different amount of powder proteins (MCI, MPI, Calcium caseinate), and maltodextrine (glucose syrup 47DE, about 2.2 kg) was added to the solution. Next, the minerals and trace elements were dissolved in water (about 160 g in 200 g of water) and added to the composition (choline chloride, magnesium hydrogen phosphate, penta-calcium triphosphate, di-potassium hydrogen phosphate, and potassium hydrogen (di)-phosphate). Next, potassium citrate (about 6 g) and a mineral mix (about 6 g) was dissolved in 100 g of water and added to the composition as fast as possible. The viscosity was determined (Viscosity 1). The solution was left to rest for a few hours. Next, the fat (about 1.6 kg of rapeseed oil and about 47 g of soy lecithin IP) was added, the batches were pasteurized for 30 seconds at 85° C. and homogenised. The viscosity was determined (Viscosity 2). Finally, varying amounts of sodium ascorbate (about 5 to 8 g) was added. The viscosity was determined (Viscosity 3). The pH of the solutions is about 6.5. Finally, the batches were sterilised for 4 minutes at 124° C. The viscosity was determined (Viscosity 4). All viscosities were determined at 20° C. in a rotational rheometer at a shear rate of 100 s$^{-1}$.

The final compositions are given in Table 1 (Example 1 to 6). The time-resolved viscosities 1 to 4 are given in Table 2. Example 7 was prepared in the same way, but only the final viscosity 4 was determined and shown in Table 2.

TABLE 2

| Viscosity (mPa · s) | Ex. 1 | Ex. 2 | Ex. 3 | Ex. 4 | Ex. 5 | Ex. 6 |
|---|---|---|---|---|---|---|
| Viscosity 1 | 182 | 179 | 270 | 212 | 126 | 199 |
| Viscosity 2 | 154 | 147 | 165 | 156 | 148 | 199 |
| Viscosity 3 | 135 | 116 | 131 | 136 | 120 | 155 |
| Viscosity 4 | 166 | 125 | 126 | 126 | 124 | 116 |

The above examples were also attempted with more than 25 mg of monovalent metal ions per gram of protein by raising these levels with the different salts. This was not possible by using Na or K as chloride salts, phosphate salts or citrate salts, or combinations of these. The products aggregated during the heating process, became pastelike and/or had a viscosity larger than 300 mPa·s.

Preparation B

Appropriate amount of MCI, MPI and caseinate were dry mixed and dissolved in excess of demineralised water at ambient temperature to a concentration of about 10 weight % of protein. Appropriate amounts of fat, carbohydrates, minerals, trace elements and vitamins (for amounts, see above: Preparation A) were added. The pH was adjusted to 6.8 with citric acid. The solution was homogenized and subsequently concentrated with the help of an evaporator to the desired nutrient concentrations (see Table 1). The product was UHT sterilized for 4 minutes at 124° C. The final product has a small particle size and a low viscosity, comparable to the compositions prepared by Preparation A.

It should be understood that various changes and modifications to the presently preferred embodiments described herein will be apparent to those skilled in the art. Such changes and modifications may be made without departing from the spirit and scope of the invention and without diminishing its advantages. It is therefore intended that such changes and modifications are covered by the appended claims.

TABLE 1

| Component (Amounts per 100 ml of product) | Example 1 | Example 2 | Example 3 | Example 4 | Example 5 | Example 6 | Example 7 |
|---|---|---|---|---|---|---|---|
| Energy | 240 kcal | 240 kcal | 240 kcal | 240 kcal | 240 kcal | 240 kcal | 240 kcal |
| Protein (En %) | 25 En % | 25 En % | 25 En % | 25 En % | 25 En % | 25 En % | 25 En % |
| Protein | 15 g | 15 g | 15 g | 15 g | 15 g | 15 g | 14.8 g |
| MCI* | 9 g | 9 g | 9 g | 11 g | 7 g | 13 g | 14.8 g |
| MPI* | 3 g | 4.5 g | 4 g | 2 g | 6 g | 0 g | 0 g |
| Ca-caseinate* | 3 g | 1.5 g | 2 g | 2 g | 2 g | 2 g | 0 g |
| Fat (En %) | 35 En % | 35 En % | 35 En % | 35 En % | 35 En % | 35 En % | 35 En % |
| Fat | 9.3 g | 9.3 g | 9.3 g | 9.3 g | 9.3 g | 9.3 g | 9.3 g |
| Carbohydrates (En %) | 40 En % | 40 En % | 40 En % | 40 En % | 40 En % | 40 En % | 40 En % |
| Carbohydrates | 24 g | 24 g | 24 g | 24 g | 24 g | 24 g | 24 g |
| Final viscosity (mPa · s at 20° C. at 100 s$^{-1}$) | 166 | 125 | 126 | 126 | 124 | 116 | 112 |
| Monovalent metal ions (Na + K) (mg/100 ml) | 128 | 131 | 130 | 128 | 131 | 126 | 146 |
| as mg/g protein | 8.6 | 8.7 | 8.7 | 8.5 | 8.7 | 8.4 | 10 |
| Divalent metal ions(Ca + Mg) (mg/100 ml) | 454 | 454 | 454 | 454 | 454 | 454 | 454 |

*Micellar Casein Isolate (MCI) contains about 89 weight % of micellar casein and whey, relative to total dry matter, with a micellar casein:whey ratio of about 95:5.
*Ca-caseinate contains about 96 weight % of casein protein, relative to total dry matter.
*Milk Protein Isolate (MPI) contains micellar casein and whey with a micellar casein:whey ratio of about 80:20.

The invention claimed is:

1. A heat-treated liquid enteral nutritional composition comprising (a) 10 to 20 g of protein per 100 ml of the composition, (b) less than or equal to 10 weight % of whey protein, and (c) between 170 and 600 mg calcium per 100 ml of the composition, in which at least 70 weight % of the protein comprises micellar casein, the total amount of monovalent metal ions in the composition is less than 25 mg/g of protein, and the viscosity of the composition is lower than 200 mPa·s as measured at a shear rate of 100 s$^{-1}$ at 20° C. using a rotational viscosity meter using a cone/plate geometry.

2. The heat-treated liquid enteral nutritional composition according to claim 1, wherein the total amount of monovalent metal ions is less than 20 mg/g of protein.

3. The heat-treated liquid enteral nutritional composition according to claim 1, wherein the total amount of monovalent metal ions is between 5 and 25 mg/g of protein.

4. The heat-treated liquid enteral nutritional composition according to claim 1, wherein the monovalent metal ions comprise sodium ions, potassium ions, or both.

5. The heat-treated liquid enteral nutritional composition according to claim 1, in which at least 80 weight % of the protein comprises micellar casein.

6. The heat-treated liquid enteral nutritional composition according to claim 1, in which the protein provides 10% to 100% of the total energy content of the composition.

7. The heat-treated liquid enteral nutritional composition according to claim 1, wherein the protein comprises at most 30 weight % of caseinate, based on the total weight of the protein.

8. The heat-treated liquid enteral nutritional composition according to claim 7, wherein micellar casein and caseinate comprise at least 95 weight % of the total protein.

9. The heat-treated liquid enteral nutritional composition according to claim 7, wherein the caseinate is a divalent ion-caseinate.

10. The heat-treated liquid enteral nutritional composition according to claim 1, further comprising fat, digestible carbohydrates, non-digestible carbohydrates, or a combination thereof.

11. The heat-treated liquid enteral nutritional composition according to claim 10, wherein the fat provides between 10 to 70% of the total energy content of the composition.

12. The heat-treated liquid enteral nutritional composition according to claim 10, wherein the fat comprises a source of long chain fatty acids.

13. The heat-treated liquid enteral nutritional composition according to claim 10, wherein the digestible carbohydrates provide between 30 to 60% of the total energy content of the composition.

14. The heat-treated liquid enteral nutritional composition according to claim 1, wherein the composition is in the form of a 125 ml unit dosage.

15. The heat-treated liquid enteral nutritional composition according to claim 1, having (a) an energy density of about 1.0 to 3.5 kcal/ml, and (b) a micellar casein to caseinate weight ratio of about 80:20 to 100:0, and comprising about 14 to 16 g of protein per 100 ml of the composition, wherein the protein provides 20 to 40% of the total energy content of the composition.

16. The heat-treated liquid enteral nutritional composition according to claim 1, having (a) an energy density of about 2.4 kcal/ml, and (b) a micellar casein to caseinate weight ratio about 80:20 to 100:0, and comprising about 15 g of protein per 100 ml of the composition, wherein:
  (i) protein provides about 25% of the total energy content of the composition;

(ii) fat provides about 35% of the total energy content of the composition; and (iii) carbohydrate provides about 40% of the total energy content of the composition.

17. A method of providing nutrition, comprising administering to a person in need thereof the nutritional composition according to claim 1.

18. The method according to claim 17, wherein the person is an elderly person, a person that is in a disease state, a person that is recovering from a disease state, or a person that is malnourished.

19. A heat-treated semi-solid enteral nutritional composition comprising 10 to 20 g of protein per 100 ml of the composition and a thickener or gelling agent, in which at least 70 weight % of the protein comprises micellar casein, and in which the total amount of monovalent metal ions in the composition is less than 25 mg/g of protein.

20. The heat-treated semi-solid nutritional composition according to claim 19, in the form of a pudding, a custard, a soup, an ice cream, and a gelly.

21. The heat-treated liquid enteral nutritional composition according to claim 1, comprising 12 to 20 g of protein per 100 ml of the composition.

22. A heat-treated liquid enteral nutritional composition, comprising (a) 10 to 20 g of protein per 100 ml of the composition, (b) between 170 and 600 mg calcium per 100 ml of the composition, wherein the protein comprises micellar casein isolate and milk protein isolate, the total amount of monovalent metal ions in the composition is less than 25 mg/g of protein, and the viscosity of the composition is lower than 200 mPa·s as measured at a shear rate of 100 s$^{-1}$ at 20° C. using a rotational viscosity meter using a cone/plate geometry.

* * * * *